United States Patent [19]
Kim et al.

[11] Patent Number: 6,048,540
[45] Date of Patent: Apr. 11, 2000

[54] ACETAMENOPHEN COMPOSITION WITH REDUCED LIVER TOXICITY

[75] Inventors: Jung Woo Kim, Seoul; Hee Jong Shin, Kyeonggi-do; Jae Soo Shin, Seoul; Min Hyo Ki, Keonggi-do, all of Rep. of Korea

[73] Assignee: Chong Kun Dang Corp., Rep. of Korea; .

[21] Appl. No.: 09/155,507

[22] PCT Filed: Jan. 24, 1998

[86] PCT No.: PCT/KR98/00017

§ 371 Date: Sep. 29, 1998

§ 102(e) Date: Sep. 29, 1998

[87] PCT Pub. No.: WO98/32434

PCT Pub. Date: Jul. 30, 1998

[30] Foreign Application Priority Data

Jan. 29, 1997 [KR] Rep. of Korea ..................... 97-2600

[51] Int. Cl.[7] ................. A61K 9/00; A61K 9/48; A61K 9/20
[52] U.S. Cl. ................ 424/400; 424/451; 424/464
[58] Field of Search .............................. 424/451, 464, 424/436, 400

[56] References Cited

U.S. PATENT DOCUMENTS

| | | | |
|---|---|---|---|
| 4,314,989 | 2/1982 | Rosen | 424/10 |
| 4,562,024 | 12/1985 | Rogerson | 264/117 |
| 4,631,284 | 12/1986 | Salpekar et al. | 514/277 |
| 5,562,919 | 10/1996 | Doty et al. | 424/464 |
| 5,716,991 | 2/1998 | Jones | 514/562 |

FOREIGN PATENT DOCUMENTS

| | | |
|---|---|---|
| 1 442 159 | 7/1976 | United Kingdom . |
| 1 463 505 | 2/1977 | United Kingdom . |
| 2 103 087 | 2/1983 | United Kingdom . |
| 2 124 078 | 2/1984 | United Kingdom . |
| WO 94/08628 | 4/1994 | WIPO . |
| WO 94/20086 | 9/1994 | WIPO . |

OTHER PUBLICATIONS

S.S. Lee et al., "Role of CYP2E1 in the Hepatotoxicity of Acetaminophen," *J. Biol. Chem*, 271:12063–12067 (1996).
V. E. Kostrubsky et al., "Acute Hepatotoxicity of Acetaminphen in Rats Treated with Ethanol Plus Isopentanol," *Biochem. Pharma.*, 20:1743–1748 (1995).
A. J. Makin et al., "Liver, Pancreas, and Biliary Tract: A 7–Year Experience of Severe Acetaminophen–Induced Hepatotoxicity (1987–1993)," *Gastroenterology*, 109:1907–1916 (1995).
H. J. Zimmerman and W. C. Maddrey, "Acetaminophen (Paracetamol) Hepatotoxicity With Regular Intake of Alcohol: Analysis of Instances of Therapeutic Misadventure," *Hepatology*, 22:767–773 (1995).

*Primary Examiner*—Todd D Ware
*Attorney, Agent, or Firm*—Heslin & Rothenberg, P.C.

[57] ABSTRACT

The present invention is related to a new analgesic composition of acetaminophen targeting decreasing of liver toxicity and releasing of hangover, which comprises aspartic acid promoting alcohol metabolism and methionine alleviating liver toxicity of acetaminophen. The analgesic combination preparation according to the present invention showed same analgesic and excellent protection effect against liver toxicity compared with the single preparation of acetaminophen, and decreased the blood concentration of alcohol and acetaldehyde causing hangover through improving metabolism rates of them. The combination preparation according to the present invention, therefore, is coincident with ideal new analgesic composition of acetaminophen having a minimized side effect and a hangover releasing effect.

13 Claims, 4 Drawing Sheets

ACETAMENOPHEN COMPOSITION WITH REDUCED LIVER TOXICITY

TECHNICAL FIELD

The present invention relates to new analgesic composition comprising acetaminophen, aspartic acid and methionine, to obtain the alleviation of liver toxicity and the release of hangover as well as an analgesic effect.

BACKGROUND ART

Acetaminophen is a typical antipyretic and analgesic agent which is used frequently instead of aspirin. However, liver toxicity of acetaminophen is recently on the rise as intensive side effect, and has been reported in many articles. The high dose administration of that induces acute liver toxicity. And especially to the patient of alcoholic liver dysfunction, a infant and indeed even a normal healthy person in the case of long-time multiple dosing, it is known that the usual dose administration of acetaminophen also induces widespread liver toxicity and can induce ophthalmic disease such as cataract. Besides, it is worried that a normal healthy person can get liver toxicity induced by acetaminophen because a modern usually takes much alcoholic drink for the release of stress coming from his place of work, etc. Acetaminophen administrated at the condition of liver function weakened by alcohol may induces severe liver toxicity with acceleration effect, and may bring about the retardation of recovery from hangover.

It gets known that the liver toxicity of acetaminophen related to medicines administered together. Alcohol and medicines of barbital family, representatively, increase severely the liver toxicity of acetaminophen through the liver enzyme induction. Especially, it was reported that only usual dose administration of acetaminophen induced a pathological change of liver cell in an alcoholic poisoning person as well as high dose administration of acetaminophen after drinking of alcohol induces severe liver toxicity (*J. Biol. Chem.*, 271(20), 12063; *Biochem. Pharmacol.*, 50(11), 1743; *Gastorenterol.*, 109(6), 1907; *Hapatol.*, 22(3), 767). At low dose, only about 2% of acetaminophen is eliminated as unmetabolized form, and most of that is eliminated as inactive metabolites of sulfonated form (20~30%), glucuronic acid conjugation (45~55%), and cysteine and mercaptouric acid conjugation (15~55%). However, liver enzyme induction agent such as alcohol and barbital, and acetaminophen of high dose increase the activity of cytochrome P-450 in liver cell and bring about production of intensive alkylation agent, that is, active metabolite N-acetly-p-benzoquinoneimine (NAPQI) as well as main metabolite, that is, inactive metabolite. NAPQI produced is inactivated through the conjugation with glutathione, but if the glutathione is depleted, NAPQI binds with —SH group of cell protein and, therefore, induces liver toxicity through alkylation or oxidation.

The agents that can alleviate liver toxicity of acetaminophen are chemicals such as cysteamine, methionine, cysteine, dimethylmercaptol, selenium, tocopherol, ascorbic acid, etc. They can alleviate liver toxicity at various efficacy range of acetaminophen. These chemicals have antioxidation effect commonly and it is proposed that liver toxicity of acetaminophen is alleviated through these antioxidation effects. However, it is known that butylhydroxytoluene, butylhydroxyanisol, etc., which are the representative antioxidants and food additives, increase liver toxicity of acetaminophen and until now the relation of the antioxidation process and the alleviation effect of liver toxicity of acetaminophen did not become clear. Recently, it is concerned about each action mechanisms of such chemicals. In said chemicals having antioxidation effect, thiol compounds (having —SH group) such as methionine, cysteamine, cysteine, dimethylmercaptol, etc. act as precursor of glutathione, and it is known that they can be used for prevention and treatment of liver toxicity of acetaminophen. These thiol compounds alleviate the liver toxicity of acetaminophen by producing glutathiones which conjugate and convert NAPQI, active metabolite of acetaminophen, into inactive metabolite.

Until now many studies, for example, patents such as WO 9,408,628, U.S. Pat. No. 4,314,989, etc. have been performed to alleviate the liver toxicity of acetaminophen. Said patents show that thiol compounds such as diarylsulfone, diarylsulfide, diarylsulfoxide, acetylcysteine, methionine sulfoxide, etc. are efficacious for prevention and treatment of liver toxicity of acetaminophen.

Aspartic acid is the medicine having the promotion effect of alcohol metabolism and facilitates the alcohol metabolism through connecting to Malate-Aspartate Shuttle of liver cell and correcting the ratio of NAD and NADH, which are coenzyme of alcohol metabolism. Alcohol is degraded to acetaldehyde by alcohol dehydration enzyme in existence of $NAD^+$, which is cofactor, or by microsomal ethanol oxidizing system (MEOS) and degradation enzyme of peroxisome in existence of NADPH. Acetaldehyde produced is also metabolized to acetic acid, as a final product, by aldehyde dehydration enzyme in existence of $NAD^+$. However, in the case of taking much alcohol, alcohol degradation enzyme is saturated and, therefore, overall alcohol metabolism becomes slow and the blood concentrations of alcohol and aldehyde increase. Especially due to the saturation of aldehyde dehydration enzyme aldehyde, which induces extensive side effects, is not able to be metabolized into acetic acid and is accumulated continuously. The acetaldehyde causes, what is called, hangover state by inducing nausea, vomiting, headache as well as liver toxicity. Moreover, in the accumulation state of acetaldehyde acetaminophen administration increases the side effect of acetaldehyde as well as liver toxicity of acetaminophen. At this point, aspartic acid acts $NAD^+$ production by connecting to Malate-Aspartate Shuttle and, therefore, does not make only alcohol degradation but also acetaldehyde metabolism possible through metabolizing acetaldehyde, which is a hangover-causing material, to acetic acid. Therefore, aspartic acid is efficacious to prevention and removal of hangover state.

DISCLOSURE OF THE INVENTION

Figure 1:
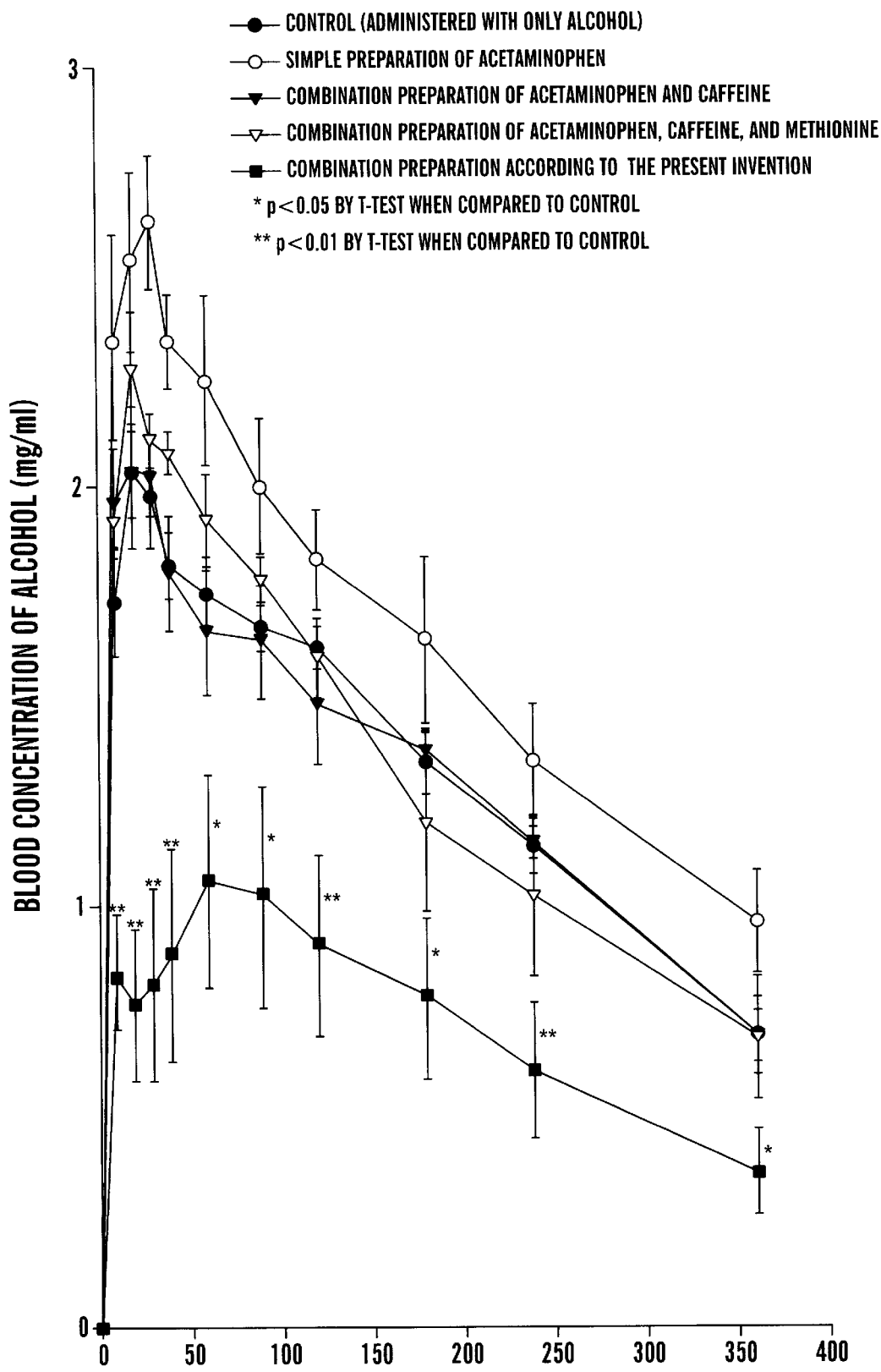
FIG. 1 shows blood concentration-time profiles of alcohol following the oral administration of comparative preparations and combination preparation according to the present invention to rats with dose of 150 mg/kg as acetaminophen.

The present invention relates to new analgesic composition.

The composition of the present invention comprises acetaminophen, aspartic acid or its pharmaceutically acceptable salts, and methionine or its pharmaceutically acceptable salts. Aspartic acid or its pharmaceutically acceptable salts is used as 0.02~2 weight part of acetaminophen, and preferred as 0.05~0.5 weight part of acetaminophen. For an usual oral dose aspartic acid is prescribed in the composition according to the present invention with 0.1~2 mg/kg, preferred with 0.25~1 mg/kg. Methionine or its pharmaceutically acceptable salts is used as 0.05~5 weight part of acetaminophen, and preferred as 0.2~2 weight part of acetaminophen. For an usual oral dose methionine is prescribed in the composition according to the present invention with 0.5~10 mg/kg, preferred with 1~5 mg/kg. Any one of caffeine, chlorpheniramine maleate or diphenhydramine can be added in the composition according to the present invention and is used as 0.01~1 weight part of acetaminophen, and preferred as 0.05~0.5 weight part of acetaminophen. For an usual oral dose they are prescribed in the composition according to the present invention with 0.1~2 mg/kg, preferred with 0.25~1 mg/kg.

The composition according to the present invention is an ideal analgesic composition which is able both to alleviate the liver toxicity of acetaminophen through the combination prescription of methionine and to dissolve a hangover state through the combination prescription of aspartic acid. To prove the superiority of the composition according to the present invention, the composition and the comparison formulations containing acetaminophen were administered separately to laboratory animals, and the prevention effects of liver toxicity and the metabolism rates of alcohol and acetaldehyde after alcohol administration were tested. The results of said tests showed that the composition according to the present invention had more excellent protection effect of liver function than the comparison formulations containing acetaminophen did and decreased the blood concentration of alcohol through increasing of alcohol metabolism rate. Therefore, it is proved that the composition according to the present invention is suited to all the purpose of the new analgesic of combination prescription, that is, prevention of liver toxicity of acetaminophen, decreasing of liver toxicity through promotion of alcohol and acetaldehyde metabolism and releasing of hangover.

The present invention is further illustrated by the following examples and experimental examples. However, the present invention is not restricted by them.

EXAMPLE 1

The components were mixed homogeneously with composition ratio of Table 1, and tablet or capsule was prepared by typical method through adding of excipients (and filling in capsule, for preparing of capsule) to comprise acetaminophen of 100 and 250 mg per tablet or capsule.

TABLE 1

Prescription examples of main components contained in tablets or capsules according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |

EXAMPLE 2

The components were mixed homogeneously with composition ratio of Table 2, and tablet or capsule was prepared by typical method through adding of excipients (and filling in capsule, for preparing of capsule) to comprise acetaminophen of 100 and 250 mg per tablet or capsule.

TABLE 2

Prescription examples of main components contained in tablets or capsules according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |
| Caffeine | 2 | 1 | 0.5 | 0.25 |

EXAMPLE 3

The components were mixed homogeneously with composition ratio of Table 3, and tablet or capsule was prepared by typical method through adding of excipients (and filling in capsule, for preparing of capsule) to comprise acetaminophen of 100 and 250 mg per tablet or capsule.

TABLE 3

Prescription examples of main components contained in tablets or capsules according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |
| Diphenhydramine | 2 | 1 | 0.5 | 0.25 |

EXAMPLE 4

The components were mixed homogeneously with composition ratio of Table 4, and then a sour and a sweet tastes were controlled by adding of citric acid and sugar (or sorbitol), etc. Suspending agent and flavor were added into the mixture, and alcohol was mixed to prepare a syrup comprising alcohol of 8.5% and acetaminophen of 30, 100 mg/ml.

TABLE 4

Prescription examples of main components contained in syrups according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |

EXAMPLE 5

The components were mixed homogeneously with composition ratio of Table 5, and then a sour and a sweet tastes were controlled by adding of citric acid and sugar (or sorbitol), etc. Suspending agent and flavor were added into the mixture, and alcohol was mixed to prepare a syrup comprising alcohol of 8.5% and acetaminophen of 30, 100 mg/ml.

TABLE 5

Prescription examples of main components contained in syrups according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |
| Caffeine | 2 | 1 | 0.5 | 0.25 |

EXAMPLE 6

The components were mixed homogeneously with composition ratio of Table 6, and then a sour and a sweet tastes were controlled by adding of citric acid and sugar (or sorbitol), etc. Suspending agent and flavor were added into the mixture, and alcohol was mixed to prepare a syrup comprising alcohol of 8.5% and acetaminophen of 30, 100 mg/ml.

TABLE 6

Prescription examples of main components contained in syrups according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |
| Diphenhydramine | 2 | 1 | 0.5 | 0.25 |

EXAMPLE 7

The components were mixed homogeneously with composition ratio of Table 7, and suppository was prepared using Witepsol by typical method through adding of excipients to comprise acetaminophen of 100, 250 mg.

TABLE 7

Prescription examples of main components contained in suppositories according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |

EXAMPLE 8

The components were mixed homogeneously with composition ratio of Table 8, and suppository was prepared using Witepsol by typical method through adding of excipients to comprise acetaminophen of 100, 250 mg.

TABLE 8

Prescription examples of main components contained in suppositories according to the present invention.

| Components | Prescriptions (unit:weight ratio) | | | |
|---|---|---|---|---|
| | (a) | (b) | (c) | (d) |
| Acetaminophen | 20 | 10 | 5 | 2.5 |
| Sodium aspartate | 1 | 1 | 1 | 1 |
| Methionine | 5 | 5 | 5 | 2.5 |
| Caffeine | 2 | 1 | 0.5 | 0.25 |

EXPERIMENTAL EXAMPLE 1

Analgesic Effect Test Using Acetic Acid-stretching (Writhing) Method

Male ICR mice weighing between 20 and 30 g were used. Fifteen mice were used as control. Ninety six mice were divided into twelve groups having 8 mice per group and twelve groups were divided into three large groups, that is, the large group to which the single preparation of acetaminophen was administered; the large group to which the combination preparation of acetaminophen and caffeine was administered; and the large group to which the combination preparation of prescription (b) of Example 2, 5 or 8 was administered. All mice were fasted during 18~24 h prior to drug administration. To prepare the preparation administered to the large group of combination preparation according to the present invention, each components was mixed with the ratio of the prescription (b) of Example 2, 5, or 8 homogeneously. To prepare the preparations administered to other large groups, each components was mixed with the same ratio of said prescription (b) homogeneously. The test preparations were suspended in 0.5% sodium carboxymethylcellulose solution, and then each test preparations equivalent to acetaminophen 30, 100, 300 or 600 mg/kg was administered orally to mice separately. After 1 h, 0.6% acetic acid solution was administered into peritoneal cavity by 0.1 ml per mouse body weight of 10 g. After the administration of acetic acid, stretching numbers were determined during 10 min, and the analgesic effects of the preparations were estimated by acetic acid-stretching (writhing) method of Koster et al.

The experimental result was shown in the following Table 9.

TABLE 9

The experimental result of analgesic effect using acetic acid-stretching method.

| Large Groups | n | Dose as acetaminophen (mg/kg) | Stretching numbers during 10 min | Pain suppression rate (%) |
|---|---|---|---|---|
| Control | 15 | 0 | 28.73 ± 1.02 | 0.00 |
| Simple preparation of acetaminophen | 8 | 30 | 28.14 ± 3.13 | 2.05 |
|  | 8 | 100 | 22.63 ± 2.07** | 21.23 |
|  | 8 | 300 | 12.00 ± 2.80** | 58.23 |
|  | 8 | 600 | 1.00 ± 0.87** | 96.52 |
| Combination preparation of acetaminophen and caffeine | 8 | 30 | 27.71 ± 1.74 | 3.55 |
|  | 8 | 100 | 25.00 ± 1.57 | 12.98 |
|  | 8 | 300 | 14.55 ± 3.84** | 49.36 |
|  | 8 | 600 | 2.63 ± 1.41** | 90.85 |
| Combination preparation of prescription (b) of Example 2, 5 or 8 | 8 | 30 | 28.86 ± 2.77 | −0.45 |
|  | 8 | 100 | 23.00 ± 1.00** | 19.94 |
|  | 8 | 300 | 15.09 ± 2.12** | 47.48 |
|  | 8 | 600 | 2.89 ± 2.02** | 89.95 |

- To control group, only 0.5% sodium carboxymethylcellulose was administered.
** ($p < 0.01$):Compared with control, it is significantly different.

In Table 9, the new analgesic combination preparation according to the present invention showed more excellent analgesic effect dose-dependently in the groups administered with doses equivalent to acetaminophen 100, 300 and 600 mg/kg separately than control did. The groups administered with doses equivalent to acetaminophen 300 and 600 mg/kg separately showed the tendency of having analgesic effect in order of single preparation of acetaminophen; combination preparation of acetaminophen and caffeine; and combination preparation of prescription (b) of Example 2, 5 or 8. But three preparations were not considered to be significantly different with each other. Therefore, in all dose experimented, said three preparations were not considered to be significantly different with each other and showed the analgesic effect of same level.

EXPERIMENTAL EXAMPLE 2

Analgesic Effect Test Using Tail-flick Method

Six male Sprague-Dawley rats weighing about 150 g were used as a group and ten groups were used. One group was control and another nine groups were divided into three large groups, that is, the large group to which the single preparation of acetaminophen was administered; the large group to which the combination preparation of acetaminophen and caffeine was administered; and the large group to which the combination preparation of prescription (b) of Example 2, 5 or 8 was administered. All mice were fasted during 18~24 h prior to drug administration. To prepare the preparation administered to the large group of combination preparation according to the present invention, each components was mixed with the ratio of the prescription (b) of Example 2, 5, or 8 homogeneously. To prepare the preparations administered to other large groups, each components was mixed with the same ratio of said prescription (b) homogeneously. The test preparations were suspended in 0.5% sodium carboxymethylcellulose solution, and then each test preparations equivalent to acetaminophen 100, 300 or 600 mg/kg was administered orally to rats separately. Using tail-flick apparatus by D'Amour-Smith method, radiation heating was irradiated to the 4 cm distance site from the end of rat tail and each onset time of tail-escaping was determined at 1, 2, 3 and 5 h after drug administration.

The experimental result was shown in the following Table 10.

TABLE 10

The experimental result of analgesic effect using Tail-flick method.

| Large Groups | n | Dose as acetaminophen (mg/kg) | Onset time (seconds) of pain response by radiation heating after administration of preparation | | | | |
|---|---|---|---|---|---|---|---|
| | | | Before administration | After 1 h | After 2 h | After 3 h | After 5 h |
| Control | 6 | 0 | 3.80 ± 0.31 | 3.95 ± 0.09 | 4.18 ± 0.10 | 3.85 ± 0.17 | 3.93 ± 0.25 |
| Simple preparation of acetaminophen | 6 | 100 | 4.17 ± 0.30 | 4.45 ± 0.43 | 4.25 ± 0.35 | 4.35 ± 0.14 | 3.50 ± 0.50 |
| | | 300 | 3.97 ± 0.18 | 4.97 ± 0.53 | 5.38* ± 0.50 | 4.27 ± 0.38 | 3.95 ± 0.15 |
| | | 600 | 3.70 ± 0.19 | 460* ± 0.23 | 5.58** ± 0.30 | 4.53** ± 0.17 | 4.33 ± 0.29 |
| Combination preparation of acetaminophen and caffeine | 6 | 100 | 3.87 ± 0.08 | 4.10 ± 0.28 | 4.20 ± 0.38 | 4.15 ± 0.29 | 3.53 ± 0.45 |
| | | 30 | 3.88 ± 0.08 | 5.42* ± 0.51 | 5.12 ± 0.67 | 4.12 ± 0.34 | 3.87 ± 0.27 |
| | | 600 | 3.57 ± 0.20 | 5.23** ± 0.22 | 5.60** ± 0.24 | 5.15** ± 0.26 | 4.20* ± 0.13 |
| Combination preparation of prescription (b) of Example 2,5 | 6 | 100 | 4.03 ± 0.20 | 4.68 ± 0.45 | 4.58 ± 0.41 | 4.32 ± 0.23 | 3.30 ± 0.37 |
| | | 300 | 3.80 ± 0.28 | 6.52* ± 1.11 | 5.78* ± 0.73 | 4.40 ± 0.31 | 4.42 ± 0.40 |

TABLE 10-continued

The experimental result of analgesic effect using Tail-flick method.

| | | | Onset time (seconds) of pain response by radiation heating after administration of preparation | | | | |
|---|---|---|---|---|---|---|---|
| Large Groups | n | Dose as acetaminophen (mg/kg) | Before administration | After 1 h | After 2 h | After 3 h | After 5 h |
| or 8 | | 600 | 3.73 ± 0.18 | 5.37** ± 0.35 | 5.93** ± 0.35 | 4.87** ± 0.19 | 4.33* ± 0.19 |

- To control group, only 0.5% sodium carboxymethylcellulose was administered.
*, **($p < 0.05$, $p < 0.01$): Compared with before-administration, it is significantly different.

In Table 10, the combination preparation according to the present invention, in the groups administered with dose equivalent to acetaminophen 300 and 600 mg/kg separately showed that onset times of pain response were prolonged remarkably. This phenomenon was dose-dependent. The groups administered with a dose equivalent to acetaminophen 100 mg/kg showed the tendency that onset time of pain response was prolonged slightly but all preparations were not considered to be significantly different with each other. The groups administered with doses equivalent to acetaminophen 300 and 600 mg/kg separately showed that the onset times of pain response of the large groups to which single preparation of acetaminophen; combination preparation of acetaminophen and caffeine; combination preparation of prescription (b) of Example 2, 5 or 8 were administered, respectively, were not significantly different with each other. In all doses experimented, all test preparations showed to have same analgesic effect. Through the overall results of analgesic effect tests using acetic acid-stretching (writhing) method and Tail-flick method, it was proved that new analgesic combination preparation showed the analgesic effect of same level with single preparation of acetaminophen and combination preparation of acetaminophen and caffeine.

EXPERIMENTAL EXAMPLE 3

The Experiment of Prevention Effect Against Liver Toxicity Through Acetaminophen-inducing Fatal Rate Test Ten male ICR mice weighing between 20 and 25 g were used as a group, and seven groups were used. The groups consisted of one control group and the test groups of the single preparation of acetaminophen; the combination preparation of acetaminophen and methionine; the combination preparation of prescription (b) of Example 1, 4 or 7; the combination preparation of acetaminophen and caffeine; the combination preparation of acetaminophen, caffeine and methionine; and the combination preparation of prescription (b) of Example 2, 5 or 8. All mice were fasted during 18~24 h prior to drug administration. To prepare the preparation administered to the group of combination preparation according to the present invention, each components was mixed with the ratio of the prescription (b) of Example 1, 2, 4, 5, 7 or 8 homogeneously. To prepare the preparations administered to other groups, each components was mixed with the same ratio of said prescription (b) homogeneously.

The test preparations were suspended in 0.5% sodium carboxymethylcellulose solution, and then each test preparations equivalent to acetaminophen 1,000 mg/kg was administered orally to mice. After 24 h, the number of dead mice was observed.

The experimental result was shown in the following Table 11.

TABLE 11

The experimental result of prevention effect against liver toxicity through acetaminophen-inducing fatal rate.

| Group | n | Body weight (g) | Dose as acetaminophen (mg/kg) | Numbers of dead animals | Fatal rate (%) |
|---|---|---|---|---|---|
| Control | 10 | 20.93 ± 0.22 | 1,000 | 0 | 0 |
| Simple preparation of acetaminophen | 10 | 21.12 ± 0.25 | 1,000 | 8 | 80 |
| Combination preparation of acetaminophen and methionine | 10 | 21.53 ± 0.42 | 1,000 | 1 | 10 |
| Combination preparation of prescription (b) of Example 1, 4 or 7 | 10 | 21.26 ± 0.27 | 1,000 | 0 | 0 |
| Combination preparation of acetaminophen and caffeine | 10 | 21.17 ± 0.44 | 1,000 | 9 | 90 |
| Combination preparation of acetaminophen, methionine and caffeine | 10 | 21.18 ± 0.35 | 1,000 | 1 | 10 |
| Combination preparation of prescription (b) of Example 2, 5 or 8 | 10 | 21.59 ± 0.33 | 1,000 | 1 | 10 |

- To control group, only 0.5% sodium carboxymethylcellulose was administered.

In Table 11, the new analgesic combination preparation according to the present invention showed fatal rate decreasing of same level with the combination preparation of acetaminophen and methionine or the combination preparation of acetaminophen, caffeine and methionine, and remarkable decreasing of fatal rate compared with the single preparation of acetaminophen and the combination preparation of acetaminophen and caffeine. Therefore, the new analgesic combination preparation according to the present invention prevent the liver toxicity induced by acetaminophen successfully.

EXPERIMENTAL EXAMPLE 4

The Experiment I of Hangover Releasing Effect Based on Pharmacokinetics of Alcohol Metabolism An experiment using the following method was performed to investigate the effect of the combination preparation according to the present invention for the alcohol metabolism rate. Six male Sprague-Dawley rats weighing between 250 and 310 g were used as a group, and five groups were used, that is, a control group (A); the group (B) of the single preparation of acetaminophen; the group (C) of the combination preparation of acetaminophen and caffeine; the group (D) of the combination preparation of acetaminophen, caffeine and methionine; and the group (E) of the combination preparation of prescription (b) of Example 2, 5 or 8. All rats were fasted during 18~24 h prior to drug administration. To prepare the preparation administered to the group of combination preparation according to the present invention, each components was mixed with the ratio of the prescription (b) of Example 2, 5, or 8 homogeneously. To prepare the preparations administered to other groups, each components was mixed with the same ratio of said prescription (b) homogeneously. The test preparations were suspended in 0.5% sodium carboxymethylcellulose solution, and then each test preparations equivalent to acetaminophen 150 mg/kg was administered orally to rats. After 30 min, alcohol of 2 g/kg was administered to all groups. Each blood samples was withdrawn at 10, 20, 30, 40, 60, 90, 120, 180, 240 and 360 min, and the blood concentration of alcohol was analyzed by gas chromatography method.

The experimental result was shown in FIG. 1.

In FIG. 1, the group (E) of the combination preparation according to the present invention showed significant ($p<0.01$) decreasing of blood concentration of alcohol compared with control group (A). However, the group (B) of single preparation of acetaminophen showed the tendency of increasing of blood concentration of alcohol compared with control group (A). The group (C) of the combination preparation of acetaminophen and caffeine, and the group (D) of the combination preparation of acetaminophen, caffeine and methionine showed almost same blood concentration of alcohol with control group (A). From the result, it became clear that, except the combination preparation containing aspartic acid according to the present invention, no comparison preparations (B, C and D) can improve the metabolism rate of alcohol taken and be expected to make release of hangover. In conclusion, it was proved that aspartic acid contained in the combination preparation according to the present invention maintains ideal effect of alcohol metabolism promotion regardless of the combination prescription with acetaminophen, caffeine and methionine, and that the combination preparation according to the present invention, therefore, is coincident with ideal new analgesic combination preparation having a decreasing effect of liver toxicity from alcohol and a hangover releasing effect as well as antipyretic and analgesic effects.

EXPERIMENTAL EXAMPLE 5

The Experiment II of Hangover Releasing Effect Based on Pharmacokinetics of Alcohol Metabolism An experiment using the following method was performed to investigate the effect of the combination preparation according to the present invention for the alcohol metabolism rate when the combination preparation according to the present invention is administered before and after alcohol administration separately. Six male Sprague-Dawley rats weighing between 250 and 310 g were used as a group, and three groups were used, that is, a control group; the group to which the combination preparation of prescription (b) of Example 2, 5 or 8 was administered before alcohol administration; and the group to which the combination preparation of prescription (b) of Example 2, 5 or 8 was administered after alcohol administration. All rats were fasted during 18~24 h prior to drug administration. The mixture with the ratio of prescription (b) of Example 2, 5 or 8 was suspended in 0.5% sodium carboxymethylcellulose solution and the suspension equivalent to acetaminophen 50 mg/kg was administered orally to the group of before-alcohol-administration and the group of after-alcohol-administration before and after 15 min from alcohol administration of 1 g/kg, respectively. The control group was also administered alcohol of 1 g/kg. Each blood samples was withdrawn at 10, 20, 30, 40, 60, 90, 120, 240 and 360 min after alcohol administration, and the blood concentration of alcohol was analyzed by gas chromatography method.

The alcohol administration was fixed in the range of am 11:00~pm 1:00, because the metabolisms and eliminations of many chemicals conjugating with alcohol are affected by life cycle and, especially, the metabolism rate of alcohol is faster in night than in day.

Figure 2:
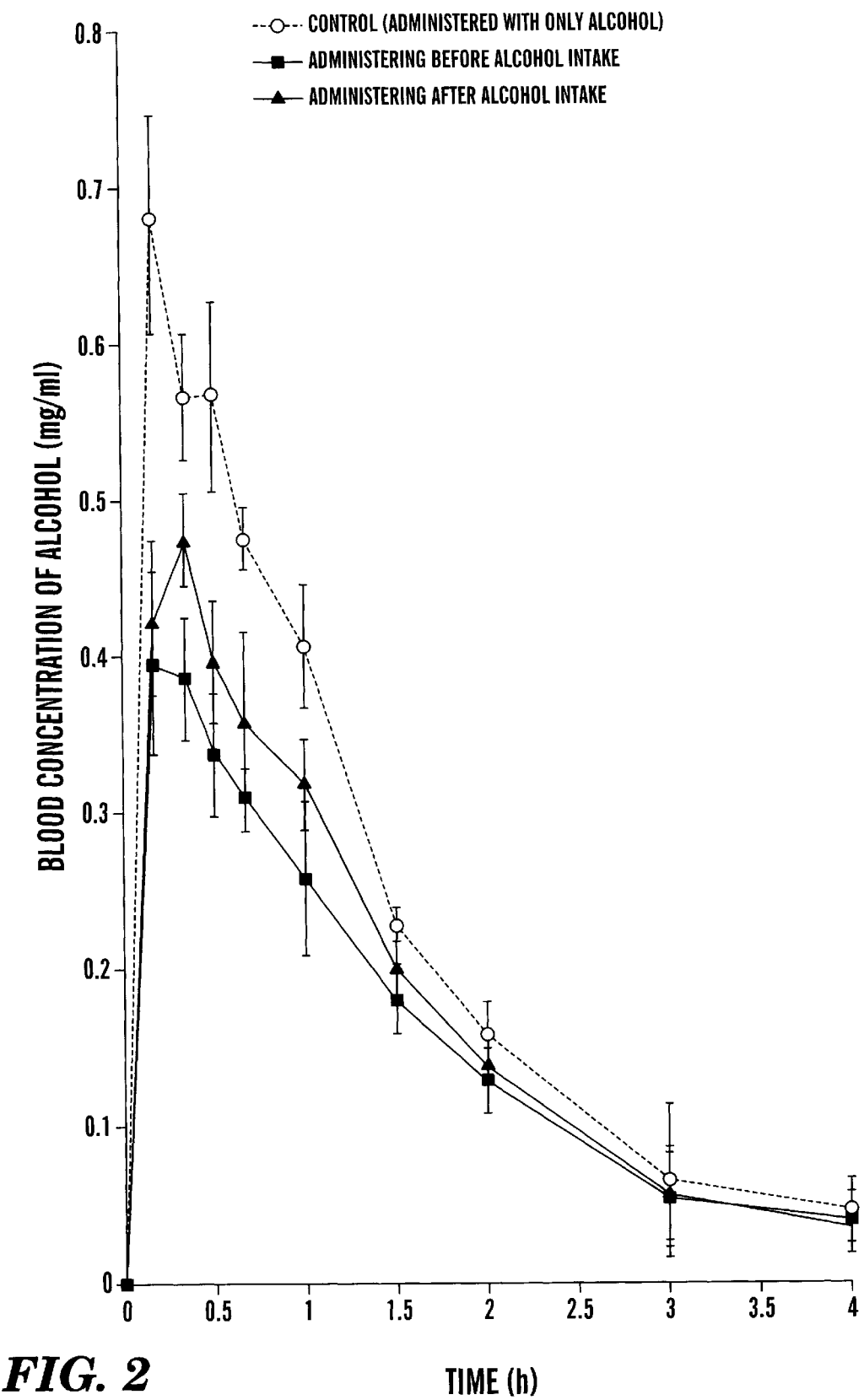
FIG. 2 shows blood concentration-time profiles of alcohol following the oral administration of combination preparation according to the present invention to rats with dose of 50 mg/kg as acetaminophen before and after alcohol intake.

The experimental result was shown in FIG. 2.

In FIG. 2, the combination preparation according to the present invention promoted an alcohol metabolism in both cases of administration before and after alcohol intake, and when the combination preparation was administered before alcohol intake, the alcohol metabolism rate was increased compared with the administration of after-alcohol-intake.

EXPERIMENTAL EXAMPLE 6

The Experiment III of Hangover Releasing Effect Based on Pharmacokinetics of Alcohol Metabolism An experiment using the following method was performed to investigate the dose dependency of the effect of the combination preparation according to the present invention for the alcohol metabolism rate. Six male Sprague-Dawley rats weighing between 250 and 310 g were used as a group, and four groups were used, that is, a control group; the group of the combination preparation of prescription (b) of Example 2, 5 or 8 equivalent to acetaminophen 75 mg/kg; the group of the same preparation equivalent to acetaminophen 150 mg/kg; and the group of the same preparation equivalent to acetaminophen 300 mg/kg. All rats were fasted during 18~24 h prior to drug administration. The mixture with the ratio of prescription (b) of Example 2, 5 or 8 was suspended in 0.5% sodium carboxymethylcellulose solution and the suspension equivalent to acetaminophen 75, 150 and 300 mg/kg was administered orally to rats separately. After 30 min, alcohol of 2 g/kg was administered to all groups. Each blood samples was withdrawn at 10, 20, 30, 40, 60, 90, 120, 240 and 360 min after alcohol administration, and the blood concentration of alcohol was analyzed by gas chromatography method.

Figure 3:
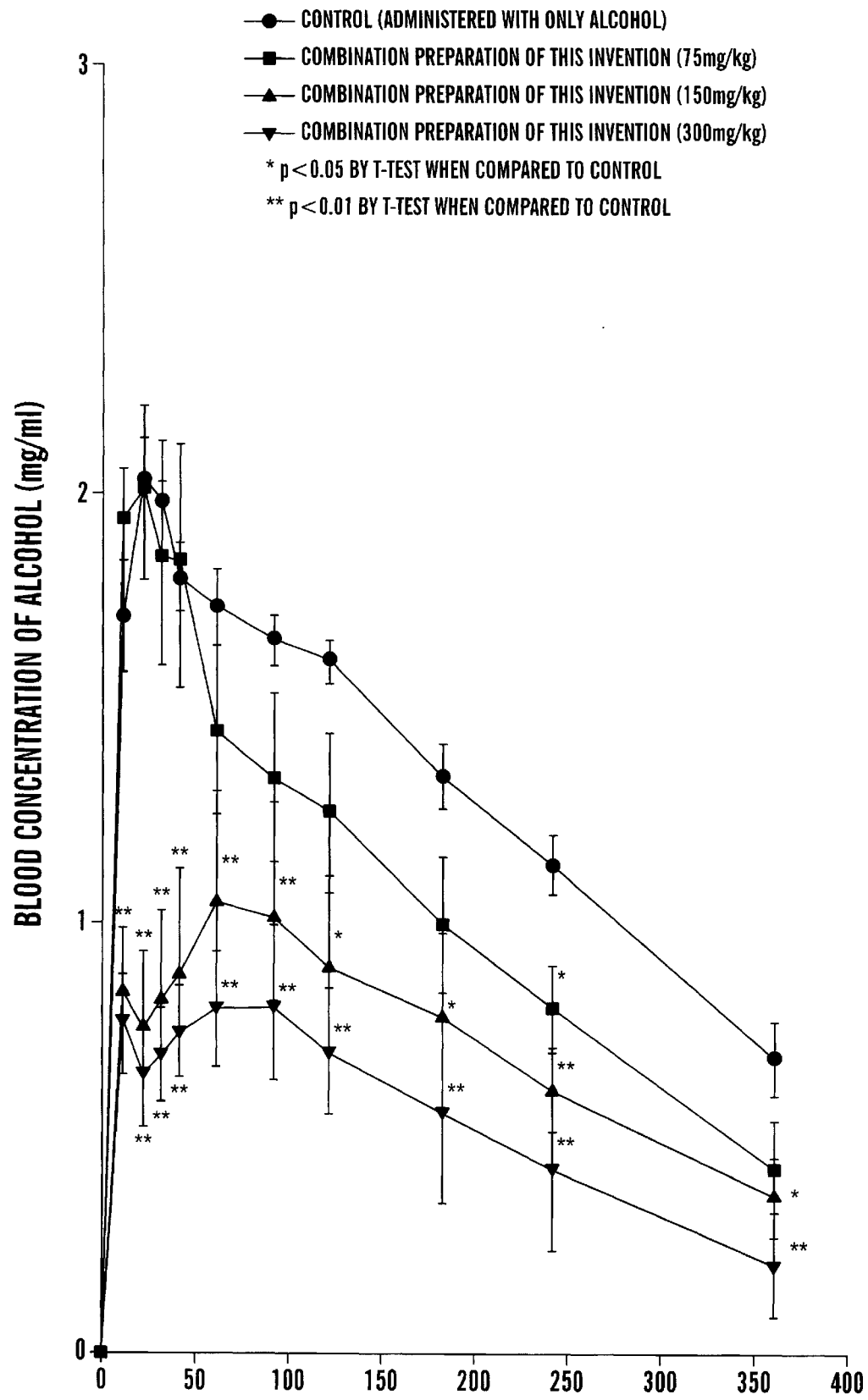
FIG. 3 shows blood concentration-time profiles of alcohol following the oral administration of combination preparation according to the present invention to rats with doses of 75, 150 and 300 mg/kg as acetaminophen.

The experimental result was shown in FIG. 3.

In FIG. 3, the group administered with the combination preparation according to the present invention of 75 mg/kg of dose showed the tendency of decreasing the blood concentration of alcohol compared with the control group, and the groups administered with doses of 150 and 300 mg/kg separately decreased that remarkably. In conclusion, it was proved that the new analgesic combination preparation according to the present invention can improve the alcohol metabolism rate dose-dependently.

EXPERIMENTAL EXAMPLE 7

The Experiment IV of Hangover Releasing Effect Based on Pharmacokinetics of Alcohol Metabolism Six male Sprague-Dawley rats weighing between 180 and 200 g were used as a group, and three groups were used, that is, a control group; the group of the combination preparation of prescription (b) of Example 2, 5 or 8 equivalent to acetaminophen 100 mg/kg; and the group of the same preparation equivalent to acetaminophen 200 mg/kg. All rats were fasted during 18~24 h prior to drug administration. The mixture with the ratio of prescription (b) of Example 2, 5 or 8 was suspended in 0.5% sodium carboxymethylcellulose solution, and the suspension equivalent to acetaminophen 100 and 200 mg/kg was administered orally to rats separately. After 30 min, alcohol of 8 g/kg was administered to all groups. Each blood samples was withdrawn at 20, 40, 80, 120, 180, 240 and 360 min after alcohol administration, and the blood concentration of acetaldehyde was analyzed by gas chromatography method.

Figure 4:
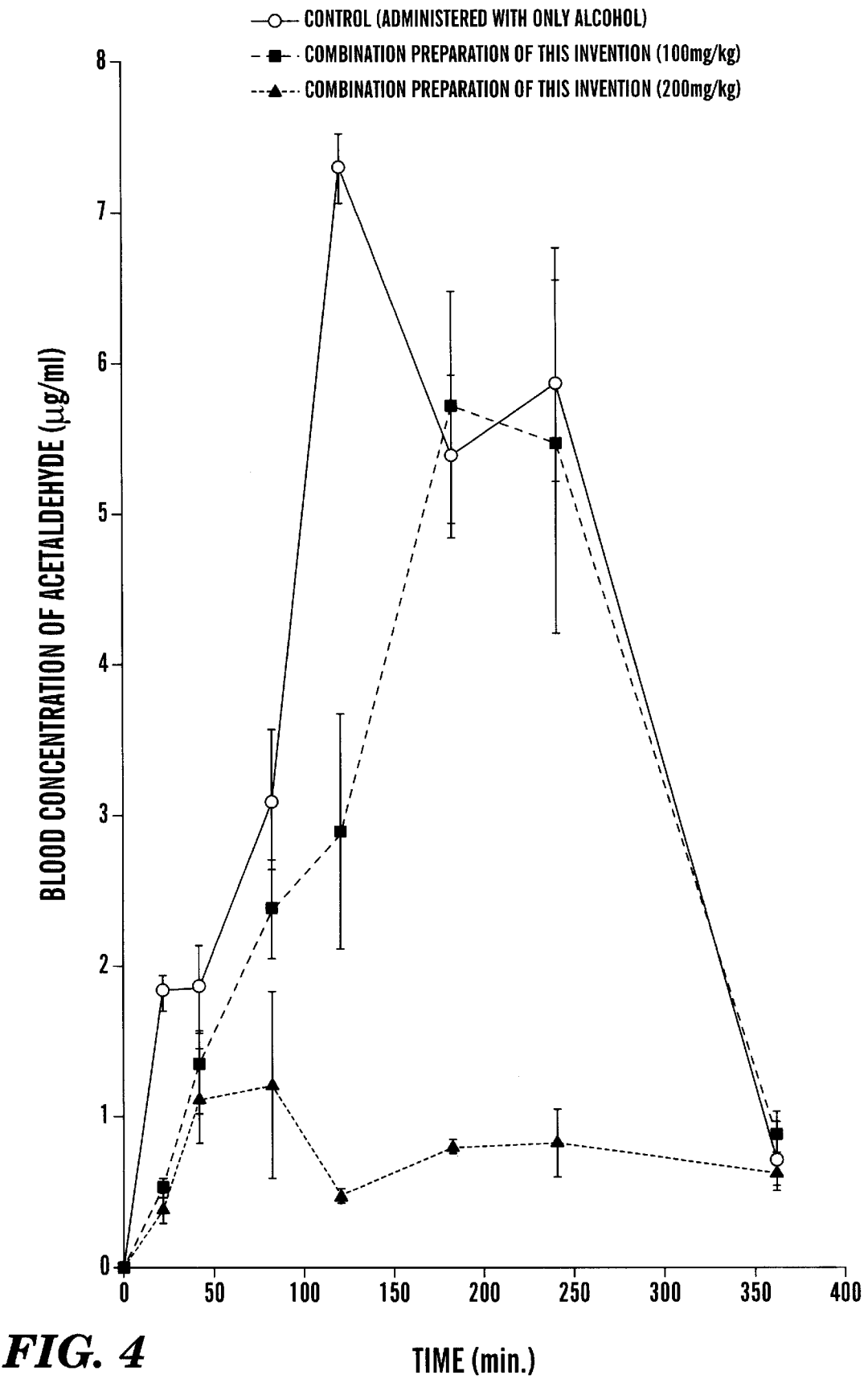
FIG. 4 shows blood concentration-time profiles of acetaldehyde following the oral administration of combination preparation according to the present invention to rats with doses of 100 and 200 mg/kg as acetaminophen.

The experimental result was shown in FIG. 4.

In FIG. 4, the combination preparation according to the present invention showed significant decreasing of acetaldehyde blood concentration compared with the control group, and it means that this combination preparation promotes the metabolism of acetaldehyde known to cause hangover. The pharmacokinetic parameters ($T_{max}$, $C_{max}$ and $AUC_{0 \to 360\ min}$) of acetaldehyde were calculated from the data and showed in Table 12.

TABLE 12

Pharmacokinetics of blood concentration of acetaldehyde.

| Group | Dose as acetaminophen (mg/kg) | n | $T_{max}$ (min) | $C_{max}$ (μg/ml) | $AUC_{0 \to 360\ min}$ (μg · min/ml) |
|---|---|---|---|---|---|
| Control | — | 3 | 120 | 7.36 ± 0.51 | 1485.20 ± 96.44 |
| Combination preparation of prescription (b) of Example 2, 5 or 8 | 100 | 3 | 180 | 5.73* ± 0.76 | 1179.27* ± 151.65 |
| Combination | 200 | 3 | 80 | 1.21** ± | 274.37** ± |

TABLE 12-continued

Pharmacokinetics of blood concentration of acetaldehyde.

| Group | Dose as acetaminophen (mg/kg) | n | $T_{max}$ (min) | $C_{max}$ (μg/ml) | $AUC_{0 \to 360\ min}$ (μg · min/ml) |
|---|---|---|---|---|---|
| preparation of prescription (b) of Example 2, 5 or 8 | | | | 0.02 | 4.71 |

- To control group, only 0.5% sodium carboxymethylcellulose was administered.
*, ** ($p < 0.05$, $p < 0.01$):Compared with control, it is significantly different.

In Table 12, the combination preparation according to the present invention decreased the blood concentration of acetaldehyde dose-dependently, and it was observed that the group administered with dose of 200 mg/kg, especially, was decreased significantly ($p<0.01$). It means that the combination preparation according to the present invention can promote the metabolism rates of both alcohol and acetaldehyde because aspartic acid increases also the metabolism rate of acetaldehyde which is the direct origin material of hangover state. Therefore, it was proved that this combination preparation has the effect of hangover releasing as well as antipyretic and analgesic effects.

EXPERIMENTAL EXAMPLE 8

Safety Investigation Through Acute Oral Toxicity Test

Acute oral toxicity test was performed by the follow method. Five male and five female Sprague-Dawley rats aged with 5 weeks and weighing between 260 and 300 g were used as a group, and four groups were used, that is, a control group and the test groups to which the combination preparation of prescription (b) of Example 2, 5 or 8 equivalent to acetaminophen 1,250 mg/kg, 2,500 mg/kg and 5,000 mg/kg was administered separately. All rats were fasted during 18~24 h prior to drug administration. The mixture with the ratio of prescription (b) of Example 2, 5 and 8 was suspended in sterilized distilled water, and the suspensions equivalent to acetaminophen 1,250 mg/kg, 2,500 mg/kg and 5,000 mg/kg as single dose were administered orally to the test groups separately. The dose ratio of 2 times was determined from pre-experiment. The number of dead animale was observed during 2 weeks from drug administration.

The experimental result was shown in the following Table 13.

TABLE 13

The result of acute oral toxicity test.

| Group | Sex | n | Administration volume (ml/kg) | Dose as acetaminophen (mg/kg) | Numbers of dead animals (Fatal rate) |
|---|---|---|---|---|---|
| Control | Male | 5 | 20 | 0 | 0 |
| | Female | 5 | 20 | 0 | 0 |

TABLE 13-continued

The result of acute oral toxicity test.

| Group | Sex | n | Administration volume (ml/kg) | Dose as acetaminophen (mg/kg) | Numbers of dead animals (Fatal rate) |
|---|---|---|---|---|---|
| Combination preparation of prescription ratio (b) of Example 2, 5 or 8 | Male | 5 | 20 | 1,250 | 0 |
|  | Female | 5 | 20 | 1,250 | 0 |
| Combination preparation of prescription (b) of Example 2, 5 or 8 | Male | 5 | 20 | 2,500 | 1 (20%) |
|  | Female | 5 | 20 | 2,500 | 0 |
| Combination preparation of prescription (b) of Example 2, 5 or 8 | Male | 5 | 20 | 5,000 | 5 (100%) |
|  | Female | 5 | 20 | 5,000 | 5 (100%) |

- To control, only sterilized distilled-water was administered orally.

As shown in Table 13, it was observed that the dead was one male rat in the group of dose of 2,500 mg/kg, and were all of ten rats in the group of dose of 5,000 mg/kg. $LD_{50}$ of the combination preparation according to the present invention calculated from the result was 2,722 mg/kg for male and 3,530 mg/kg for female.

EXPERIMENTAL EXAMPLE 9

Safety Investigation Through Subacute Oral Toxicity Test

Subacute oral toxicity test was performed by the follow method. Ten male and ten female Sprague-Dawley rats aged with 5 weeks and weighing between 260 and 300 g were used as a group, and three groups were used, that is, the group of the combination preparation of prescription (b) of Example 2, 5 or 8 equivalent to acetaminophen 40 mg/kg; the group of the same preparation equivalent to acetaminophen 160 mg/kg; and the group of the same preparation equivalent to acetaminophen 640 mg/kg. Twenty male and twenty female rats were used as a control group. All rats were fasted during 18~24 h prior to drug administration. The mixture with the ratio of prescription (b) of Example 2, 5 and 8 was suspended in sterilized distilled water, and the suspensions equivalent to acetaminophen 40, 160 and 640 mg/kg as single dose per one day were administered orally to the test groups separately for 4 weeks. The dose ratio of 4 times was determined from pre-experiment. A general symptoms, death, weight change, and amounts of feed and water intake were observed with more times than one per day. A eye, a urine, a blood and a blood-biological tests were performed simultaneously. In experiment closing, toxicological changes such as organ weight measurement, pathologic histology test etc. were checked up through autopsy.

The experimental result was shown in the following Table 14.

TABLE 14

The result of subacute oral toxicity test.

| Group | Sex | n | Administration volume (ml/kg) | Dose as acetaminophen (mg/kg) | Days of weight change | General symptoms |
|---|---|---|---|---|---|---|
| Control | Male | 20 | 10 | 0 | 0 | 0 |
|  | Female | 20 | 10 | 0 | 0 | 0 |
| Combination preparation of prescription (b) of Example 2, 5 or 8 | Male | 10 | 10 | 40 | 0 | 0 |
|  | Female | 10 | 10 | 40 | 0 | 0 |
| Combination preparation of prescription (b) of Example 2, 5 or 8 | Male | 10 | 10 | 160 | 0 | 0 |
|  | Female | 10 | 10 | 160 | 0 | 0 |
| Combination preparation of prescription (b) of Example 2, 5 or 8 | Male | 10 | 10 | 640 | 3–28 | Eye fluid congelation: 1 case |
|  | Female | 10 | 10 | 640 | 7–28 | Depilation: 1 case |

- To control, only sterilized distilled-water was administered orally.

As shown in Table 14, a dark red congelated material around eye was observed in one male rat of the group administered with the combination preparation of prescription (b) of Example 2, 5 and 8 equivalent to acetaminophen 640 mg/kg at 12 days from drug administration. Depilation was observed in one female rat of said group at 18 days from drug administration. In both female and male rats of said group, the decreasing of feed intake was observed and, when drug administration was stopped after 4 weeks, the change showing their recovery was observed. In a observation of other general symptoms, a blood and a blood-biological tests, autopsy and pathologic histology test, no change deviated from ordinary range due to administration of test preparation was identified. Only organ weight was decreased slightly. However, this phenomenon seemed to be not caused by side effect of test preparation but due to decreasing of body weight. In conclusion, the combination preparation according to the present invention has safe dose of 160 mg/kg and certain toxic dose was estimated as 640 mg/kg of dose, in which inhibition of body weight increasing was induced.

EXPERIMENTAL EXAMPLE 10

Stability Test

The preparation of prescription (b) of Example 2 was put into closed container and stored in room temperature, 40° C. and 50° C. for 6 months separately. Each samples was withdrawn at 0, 1, 3, 4 and 6 months, and tested for appearance, disintegration and content. It's appearance was observed with the naked eye. The disintegration test was performed according to USP XXIII disintegration procedure, and water of 37° C. was used as disintegration medium. The content test was performed using high performance liquid chromatography (HPLC) and amino acid analysis apparatuses.

In the result, all preparations stored in various condition showed no change of appearance and the complete disintegration within 12 min. The result of content test was showed in Table 15.

TABLE 15

The content change of combination preparation of prescription (b) of Example 2 according to storage condition.

| | Storage temperature | Initial | After 1 month | After 3 month | After 4 month | After 6 month |
|---|---|---|---|---|---|---|
| Acetaminophen | Room temperature | 101.7 | 99.70 | 101.05 | 99.08 | 99.3 |
| | 40° C. | 101.7 | 98.65 | 100.75 | 99.90 | 98.5 |
| | 50° C. | 101.7 | 101.86 | 99.30 | 100.3 | 98.1 |
| Sodium L-aspartate monohydrate | Room temperature | 101.0 | 95.32 | 97.84 | 100.77 | 97.49 |
| | 40° C. | 101.0 | 94.20 | 98.36 | 99.21 | 96.26 |
| | 50° C. | 101.0 | 93.40 | 89.88 | 82.14 | 83.46 |
| DL-Methionine | Room temperature | 99.7 | 98.34 | 97.04 | 98.88 | 97.01 |
| | 40° C. | 99.7 | 98.28 | 98.86 | 95.86 | 96.34 |
| | 50° C. | 99.7 | 98.37 | 91.36 | 96.52 | 93.22 |
| Caffeine anhydrous | Room temperature | 100.2 | 99.92 | 99.08 | 100.04 | 99.53 |
| | 40° C. | 100.2 | 98.48 | 98.48 | 99.12 | 99.25 |
| | 50° C. | 100.2 | 102.52 | 97.24 | 102.0 | 98.79 |

Shelf life (the time that a content maintains more than 90% of initial at 25° C.) of each components was calculated from the content of that showed in Table 15 with Arrehnius equation. The shelf lifes of acetaminophen, aspartic acid, methionine and caffeine were 35.94, 33.86, 35.64 and 89.84 months, respectively. It means that the preparation of prescription (b) of Example 2 is stable for more than 2 years.

What is claimed is:

1. An analgesic composition consisting essentially of:
   a) acetaminophen;
   b) aspartic acid or a pharmaceutically acceptable salt thereof, present from about 0.02 to about 2 parts per part by weight of acetaminophen; and
   c) methionine or a pharmaceutically acceptable salt thereof, present from about 0.05 to about 5 parts per part by weight of acetaminophen.

2. An analgesic composition according to claim 1 wherein said aspartic acid or a pharmaceutically acceptable salt thereof is present from about 0.05 to about 0.5 parts per part by weight of acetaminophen and said methionine or a pharmaceutically acceptable salt thereof is present from about 0.2 to about 2 parts per part by weight of acetaminophen.

3. An analgesic composition according to claim 1 further comprising one or more of caffeine, chlorpheniramine maleate and diphenhydramine.

4. An analgesic composition according to claim 3 wherein said one or more of caffeine, chlorpheniramine maleate and diphenhydramine is present from about 0.01 to about 1 part per part by weight of acetaminophen.

5. An analgesic composition according to claim 4 wherein said one or more of caffeine, chlorpheniramine maleate and diphenhydramine is present from about 0.05 to about 0.5 parts per part by weight of acetaminophen.

6. An analgesic composition according to claim 1 adapted for oral or rectal administration.

7. An analgesic composition according to claim 6 adapted for oral administration as a tablet, capsule or syrup.

8. A method of providing analgesic relief, said method comprising administering to a patient in need of such relief, an analgesic composition consisting essentially of an amount of acetaminophen, aspartic acid or a pharmaceutically acceptable salt thereof, present from about 0.02 to about 2 parts per part by weight of acetaminophen, and methionine or a pharmaceutically acceptable salt thereof, present from about 0.05 to about 5 parts per part by weight of acetaminophen.

9. A method according to claim 8 wherein said analgesic composition is administered orally.

10. A method according to claim 9, wherein the amount of said aspartic acid or a pharmaceutically acceptable salt thereof administered is between 0.1 and 2 mg per kg and the amount of said methionine administered is between 0.5 to 10 mg per kg.

11. A method according to claim 10 wherein the amount of said aspartic acid or a pharmaceutically acceptable salt thereof administered is between 0.25 to 1 mg per kg and the amount of said methionine administered is between 1 to 5 mg per kg.

12. A method according to claim 8 wherein said analgesic composition is administered rectally.

13. A method according to claim 8 further characterized in that said analgesic composition further comprises one or more of caffeine, chlorpheniramine maleate and diphenhydramine.

* * * * *